US012502098B1

(12) United States Patent
Torkelson et al.

(10) Patent No.: US 12,502,098 B1
(45) Date of Patent: Dec. 23, 2025

(54) PATIENT MONITORING SYSTEM

(71) Applicant: US Patent Care Products, LLC, Tulsa, OK (US)

(72) Inventors: Jonathan Douglas Torkelson, Tulsa, OK (US); James Patrick Lovely, Tulsa, OK (US)

(73) Assignee: US Patent Care Products, LLC, Tulsa, OK (US)

( * ) Notice: Subject to any disclaimer, the term of this patent is extended or adjusted under 35 U.S.C. 154(b) by 233 days.

(21) Appl. No.: 18/205,315

(22) Filed: Jun. 2, 2023

Related U.S. Application Data

(60) Provisional application No. 63/348,331, filed on Jun. 2, 2022.

(51) Int. Cl.
*A61B 5/11* (2006.01)
*A61B 5/00* (2006.01)
*G08B 21/04* (2006.01)

(52) U.S. Cl.
CPC .......... *A61B 5/1117* (2013.01); *A61B 5/0002* (2013.01); *A61B 5/6892* (2013.01); *A61B 5/7405* (2013.01); *A61B 5/742* (2013.01); *A61B 5/746* (2013.01); *G08B 21/0415* (2013.01); *G08B 21/0461* (2013.01); *A61B 2562/0247* (2013.01)

(58) Field of Classification Search
CPC ..... A61B 5/1117; A61B 5/1115; A61B 5/002; A61B 5/0002; A61B 5/6892; A61B 5/7405; A61B 5/742; A61B 5/746; A61B 2562/0247; A61B 2562/164; A61F 13/42; G08B 21/0415; G08B 21/0461; G08B 21/22
See application file for complete search history.

(56) References Cited

U.S. PATENT DOCUMENTS

| | | | | |
|---|---|---|---|---|
| 4,175,263 | A * | 11/1979 | Triplett | A61B 5/1116 340/666 |
| 4,484,043 | A * | 11/1984 | Musick | A61B 5/1115 200/86 R |
| 5,410,297 | A * | 4/1995 | Joseph | G08B 21/22 340/573.7 |
| 5,962,118 | A * | 10/1999 | Burgess | E05F 15/44 264/45.3 |
| 7,924,163 | B1 | 4/2011 | Long et al. | |
| 8,416,084 | B2 * | 4/2013 | Beltmann | A61B 5/6889 340/539.1 |
| 10,159,607 | B2 * | 12/2018 | Monson | A61B 5/6804 |
| 10,517,511 | B2 * | 12/2019 | Lin Charna | G08B 21/22 |
| 10,692,346 | B2 | 6/2020 | Carr | |
| 10,898,392 | B2 * | 1/2021 | Mancini | A61F 13/42 |
| 11,210,922 | B2 | 12/2021 | Carr et al. | |

(Continued)

*Primary Examiner* — Adnan Aziz
(74) *Attorney, Agent, or Firm* — GableGotwals; David G. Woodral

(57) ABSTRACT

A pressure sensitive pad has at least one internal electrical contact indicating presence of a patient on the pad when the electrical contact is closed. An internal control circuit electrically connected to the at least one contact to detect closure of the contact and an internal wireless transceiver is used by the control circuit to broadcast a signal indicating presence and absence of the patient. A wireless control unit may receive the signal and generate alarms in response thereto.

18 Claims, 7 Drawing Sheets

(56) References Cited

U.S. PATENT DOCUMENTS

| | | | | |
|---|---|---|---|---|
| 2001/0001237 | A1* | 5/2001 | Stroda | A61B 5/1117 600/595 |
| 2010/0249881 | A1* | 9/2010 | Corndorf | A61N 1/37276 607/60 |
| 2010/0253504 | A1* | 10/2010 | Lliteras | G08B 25/001 340/539.11 |
| 2012/0119912 | A1* | 5/2012 | Ortega | G08B 21/0461 340/573.5 |
| 2013/0281886 | A1* | 10/2013 | Meyers | A61B 5/103 600/587 |
| 2014/0221876 | A1* | 8/2014 | Eddy | A61B 5/6892 600/595 |
| 2017/0236398 | A1* | 8/2017 | Eddy | A61B 5/6892 340/573.5 |
| 2018/0021184 | A1* | 1/2018 | Monson | H01Q 9/0457 340/573.5 |
| 2018/0125413 | A1* | 5/2018 | Smith, Jr. | A61B 5/7282 |
| 2018/0125433 | A1* | 5/2018 | Ferber | A61B 5/743 |
| 2019/0046084 | A1* | 2/2019 | Kilcran | A61F 13/42 |
| 2019/0051137 | A1* | 2/2019 | Kilcran | G08B 25/10 |
| 2020/0230008 | A1* | 7/2020 | Newham | A61B 5/6894 |
| 2020/0261279 | A1* | 8/2020 | Weidman | A61G 7/00 |
| 2020/0320843 | A1* | 10/2020 | Carr | A61B 5/1117 |
| 2020/0342746 | A1* | 10/2020 | Hess | G08B 25/10 |
| 2021/0310891 | A1* | 10/2021 | Smith, Jr. | G01L 1/20 |
| 2022/0054047 | A1* | 2/2022 | Kilcran | A61B 5/1115 |
| 2022/0233382 | A1* | 7/2022 | Williams | A61G 7/0528 |
| 2024/0074677 | A1* | 3/2024 | Thomas | A61B 5/6892 |

* cited by examiner

PATIENT MONITORING SYSTEM

CROSS-REFERENCE TO RELATED CASES

This application claims the benefit of U.S. provisional patent application Ser. No. 63/348,331, filed on Jun. 2, 2022, and incorporates such provisional application by reference into this disclosure as if fully set out at this point.

FIELD OF THE INVENTION

This disclosure relates to the medical care field in general and, more specifically, to a system and method for monitoring patient location.

BACKGROUND OF THE INVENTION

It is frequently desirable to monitor whether a patient in a hospital or other treatment setting is in an expected location. It is advantageous for medical personnel to be alerted quickly if a patient has fallen from a bed or chair, for example. It may also be advantageous to know if an otherwise ambulatory patient has been gone from a bed or chair for an extended time (potentially indicating non-fall related issues, or cognitive/memory problems).

What is needed is a system and method for addressing these and related problems.

SUMMARY OF THE INVENTION

The invention of the present disclosure, in one aspect thereof, comprises a system for monitoring presence of a patient at a location. The system includes at least one pressure sensitive pad comprising at least one internal electrical contact indicating presence of a patient on the pad when the electrical contact is closed, an internal control circuit electrically connected to the at least one contact to detect closure of the contact, an internal wireless transceiver used by the control circuit to broadcast a signal indicating presence and absence of the patient based on the closure of the at least one contact; and an external cover sealing the at least one internal electrical contact, the internal control circuit, and the internal wireless transceiver together inside the cover.

In some embodiments the at least one internal electrical contact comprises a plurality of internal electrical contacts. The system may include an internal foam layer defining an opening containing the at least one internal electrical contact. The system may have an internal battery inside the external cover. In some cases, the external cover does not pass any wires therethrough.

The system may further comprise a wireless control unit receiving the signal broadcast from the at least one pressure sensitive pad and indicating an alarm when the pressure sensitive pad indicates the absence of the patient. The wireless control unit may include a microcontroller and a wireless transceiver, the microcontroller receiving the signal broadcast from the at least one pressure sensitive pad via the wireless transceiver and indicating the alarm. In some cases, the at least one pressure sensitive pad has a paired state and an unpaired state respecting the wireless controller, and the at least one pressure sensitive pad, when unpaired, broadcasts a connection request signal when the at least one internal electrical contact is closed.

The wireless controller may have a first pairing mode wherein it receives the connection request signal from the at least one pressure sensitive pad and broadcasts a connection response signal back to the at least one pressure sensitive pad indicating an identification of the wireless controller and an operating channel.

The at least one pressure sensitive pad may store the identification of the wireless controller and the operating channel and enter a sleep mode for a predetermined period of time. In some cases, after the predetermined period of time, the at least one pressure sensitive pad broadcasts to the wireless controller a signal indicating presence and absence of the patient based on the closure of the at least one contact using the identification of the wireless controller and the operating channel.

The wireless controller may receive signals from multiple pressure sensitive pads, each pressure sensitive pad broadcasting a separate respective signal indicating presence and absence of the patient based on the closure of the at least one internal electrical contact. In some cases, the wireless controller can be reset to determine an identification of the wireless controller by selecting a random identification that does not correspond to any identifications received wirelessly from any other wireless controllers.

In some cases, the wireless controller selects a wireless channel for communication with the at least one pressure sensitive pad by scanning available channels and selecting among the available channels with a lowest broadcast energy.

The alarm may comprise an audible alarm. The alarm may comprise an alert signal sent electronically from the wireless control unit. The alarm may comprise a visible light and/or a light visible to the patient.

The system may comprise a wireless control unit receiving the signal broadcast from the at least one pressure sensitive pad and illuminating a light in proximity to the patient in response thereto.

The invention of the present disclosure, in another aspect thereof, comprises a system for monitoring presence of a patient. The system includes a sealed pressure sensitive pad containing an internal power supply, an internal controller, and an internal contact switch contained in an opening in an internal foam layer such that weight of a patient on the pressure sensitive pad signals presence of the patient to the controller, the controller intermittently broadcasting a signal indicating presence or absence of the patient. The system includes a wireless control unit receiving the signal indicating presence of absence of the patient and producing an alarm when the signal indicates absence of the patient. The sealed pressure sensitive pad is impervious to bodily fluids and does not have any external openings for wiring. The signal indicates absence or presence of a patient.

DETAILED DESCRIPTION OF THE PREFERRED EMBODIMENTS

Figure 1:
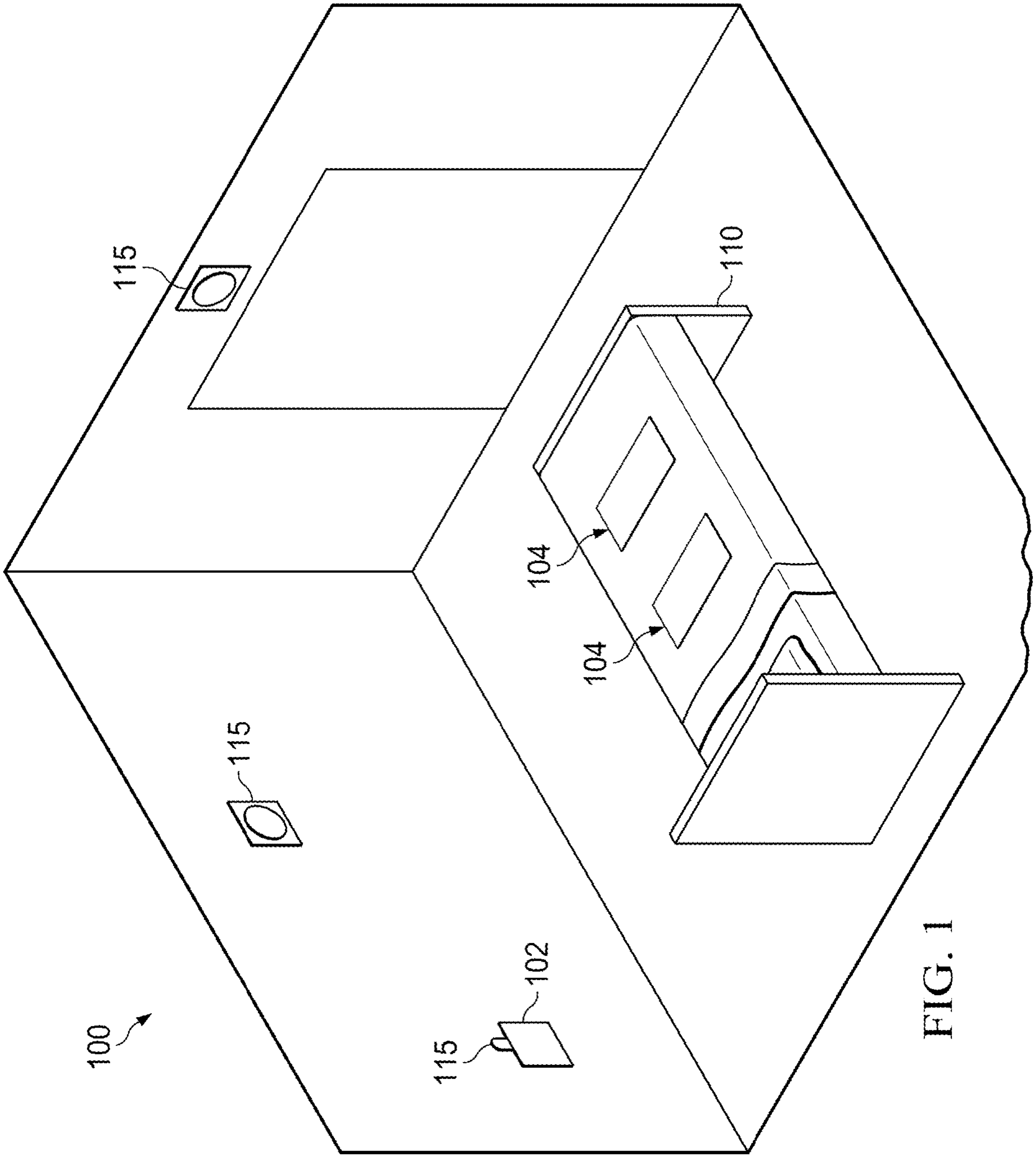
FIG. 1 is a perspective view of a patient monitoring system according to aspects of the present disclosure.

Referring now to FIG. 1 is a perspective view of a patient monitoring system 100 according to aspects of the present disclosure is shown. In various embodiments, the system 100 comprises one or more pads 104 that monitor patient location or position. The pads 104 may be pressure sensitive such that weight of a patient or lack thereof indicates to the pad whether the patient is present. The system 100 may also comprise a wireless control unit 102. The pads 104 can communicate wirelessly to the control unit 102 indicating whether or not a patient is on the pad(s) 104. Pads 104 may be placed in a variety of locations including, but not limited to, a bed, 110, under a toilet seat, or a chair (not shown). Pads 104 may be thin and unobtrusive to avoid patient discomfort. Pads may be constructed of materials that are resistant to liquids or bodily fluids, or otherwise constructed so that they will not fail to operate properly in a variety of conditions.

Pads 104 may have a limited lifespan, or at least a shorter lifespan than the wireless control unit 102. Additionally, pads 104 may become soiled or otherwise need to be changed or exchanged (e.g., for new patients). The pads may utilize a coin cell type battery such as a CR2032. Pads may not transmit continuously, in order to save power. In some embodiments, pads periodically “wake up,” send out data related to patient presence on the pad, if available, and then return to a low power state.

As described further below, the wireless control unit 102 may detect or receive wirelessly that a patient is no longer present on the associated pad(s) 104. In response, a notification can be sent (e.g., to a nurses’ station) or an alarm can be sounded. In some cases, an alarm may not be needed, or may not be immediately needed. A light 115 may illuminate the room or location where the wireless control unit is installed. The light 115 may be a dim light or a night light. The light 115 may provide sufficient illumination to allow a patient to safely see their way to the restroom or a main light switch on a wall, for example. As shown in FIG. 1, light 115 may be integrated with wireless control unit 102, may be a separate light in the patient’s room that will illuminate when an alarm occurs, or may be located outside of a patient’s room, e.g., above the door for providing notification to nursing staff, e.g., by blinking red or another color, or by illuminating. In other embodiments, the wireless control unit 102 may control room lighting directly or otherwise control dimmed or bright lighting that may be remote from the control unit 102. Control of lighting may occur wirelessly (e.g., via MiWi, Bluetooth, or other protocol) or via a wired connection or relay. In some cases, a light will remain on until the patient returns to the pad 104 (e.g., has returned to bed) or until a nurse or other caregiver has attended to the patient and manually turns off the light (e.g., via a control on the wireless control panel 102 or elsewhere).

In one embodiment, wireless control unit 102 includes a capacitor 103 that stores energy. If the wireless control unit 102 is powered off during monitoring, for any reason, and if any sensor tracked by wireless control unit 102 is in a closed state, wireless control unit 102 will emit an alarm signal. Capacitor 103 will have stored sufficient energy to allow the control unit to send the alarm, e.g., will have enough energy stored to send a signal to a nurse call system and to wireless recipients.

Figure 2:
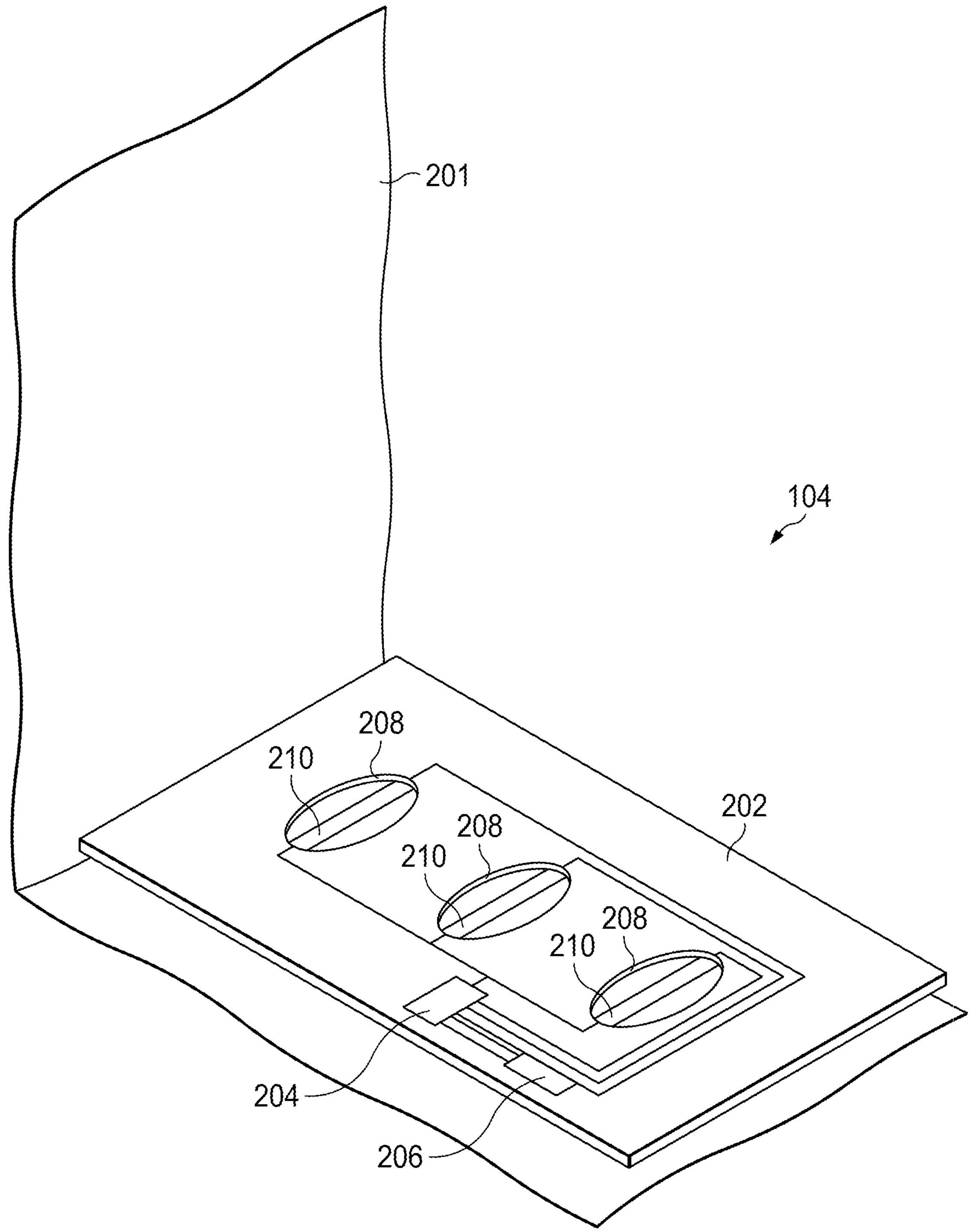
FIG. 2 is a perspective view of an interior of a pad for use with the system of FIG. 1.

Referring now to FIG. 2, a perspective view of an interior of a pad 104 for use with the system of FIG. 1. In some embodiments, the pads 104 utilize a thin foam interior 202 with openings 208 defined therein. More or fewer openings 208 may be utilized than shown. Additionally, size and shape may vary so long as the openings 208 provide location and retention for a number of contacts or switches 210. In one embodiment, wireless control unit 102 is provided with a switch to set to either state.

When a patient is present on the pad 104, one or more of the sets of contacts or switches 210 closes, thereby indicating to a monitoring circuit 204 within the pad 104 that the pad 104 is occupied. The switches 210 may be normally open but the system can also be adapted to use normally closed switches.

The pad 104 may have an exterior cover 201 or other layers covering the foam interior layer 202. For purposes of illustration, the cover 201 is shown open. The cover 201 may be a replaceable cover, or it may be intended to last the lifetime of the pad 104. The cover 201 can comprise multiple layers. The cover 201 may have a fabric or fabric-like feel and appearance on the outside thereof. The cover 201 may be resilient against liquids or provide an absolute barrier against liquids to protect internal components. The cover 201 may be formed of a single piece of material or formed from multiple pieces with joining edges that are sewn, glued, electronically welded, or otherwise securely sealed. In some embodiments, when the cover 201 has been closed on or over internal components of the pad 104, there are no openings or passages in or out of the pad (for wires, for example) to increase integrity of the pad 104 against harm from bodily fluids or other fluids. When a patient is present on the pad 104 the weight of the patient is sufficient to close one or more of the switches 210 even with the cover 201 present. To that end, thickness of the pad 104 and size of the openings may be selected in concert with the material(s) comprising the cover 201 to ensure closure of switches 210 under expected patient weights.

The open or closed state of switches 210 may be monitored by a monitoring circuit 204. Monitoring circuit 204 may comprise a microprocessor, a microcontroller, or a system on a chip device capable of implementing the necessary monitoring and network communication required by the system 100. According to various embodiments, the pads 104 may be based on a Microchip SAMR30 device or another suitable device. A battery 206, or multiple batteries, may be retained in the foam layer 202 or elsewhere for powering the pad 104. Although monitoring circuit 204 and battery 206 are shown inside of pad 104 in FIG. 2, either monitoring circuit 204, battery 206 or both may be located inside or outside of pad 104. An advantage of locating monitoring circuit 204 and/or battery 206 outside of pad 104 is that monitoring circuit 204 and battery 206 could be reusable, i.e., retained and plugged in a replacement pad 104 if desired.

In one embodiment, light 115 located in the room, outside the room, and above the patient door, and/or an affixed light emitted by wireless control unit 102, when pad 104 detects an absence of weight on pad 104, i.e., switch 210 is open, and sends a signal to wireless control unit 102 for broadcast, several things occur:

1) A local alarm may be emitted by wireless control unit 102. Local emission of an alarm may be determined by nursing staff and a switch within control unit 102 is set to, generally, on or off.
2) An alarm signal will be sent to the nurse call station.
3) Light 115 outside a patient's room will illuminate.
4) Light 115 in the patient's room will illuminate if the room is otherwise dark.

The local alarm, the alarm sent to the nurse call station, any related external lights will cancel (turn off) and broadcast connections, generally, and communications sent via Bluetooth and MiWi will cease when one of two things happens:

1) The patient's weight returns to pad 104, i.e., pad switch 210 is closed.
2) The caregiver attends to the patient and cancels the local alarm and the alarm set to the nurse call station, and broadcast communication.

In some embodiments, the system 100 utilizes a low power, low data addressable network. Pads 104 therefore may not have need to send large amounts of data. Apart from addressing the network overhead, an indication of patient presence or patient absence may be sufficient. In some embodiments, the basis of the system is MiWi also known as an IEEE 802.15.14 network.

Figure 3:
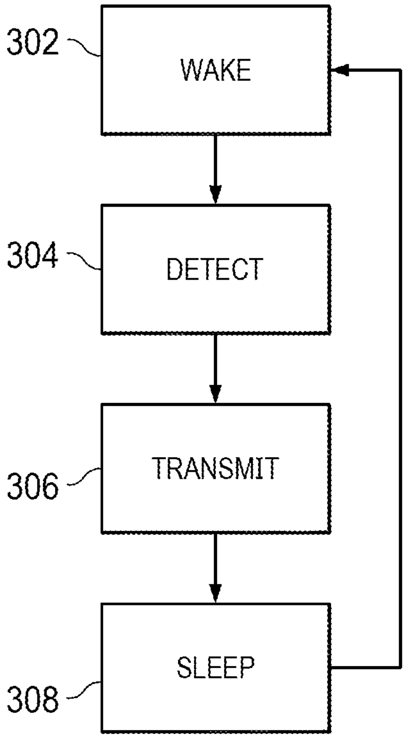
FIG. 3 is a flow chart indicating functional operation of a pad when in use.

Referring now to FIG. 3, a flow chart indicating functional operation of a pad 104 when in use. When a pad 104 is paired and operational, its function may be somewhat linear as shown. When a controller associated with the control circuit 204 wakes at step 302, it detects whether switches 210 are closed (e.g., whether a patient is present) at step 304. Where multiple switches 210 are provided, closure of single switch 210 may be sufficient to indicate presence of a patient. On the other hand, the control circuit 204 can be programmed or implemented such that two or more, or all, switches 210 must be closed to indicate a patient presence. This may depend on the size of the pad 104, the relative location of switches 210, or other factors. The gathered information (e.g., patient presence or absence) may be transmitted to the wireless controller 102 step 306, following which the pad 104 re-enters a sleep state at step 308. One of skill in the art will appreciate there are many variations on how a low power, low data pad can operate within the scope of the present disclosure.

Figure 4:
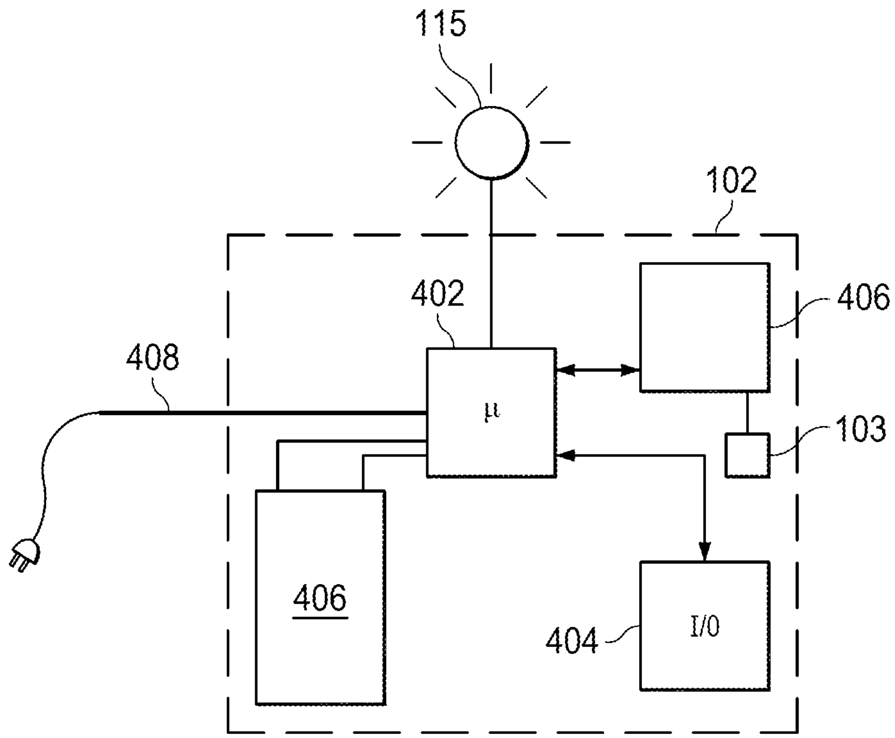
FIG. 4 is a simplified schematic of a wireless control unit for use with the system of FIG. 1.

Referring now to FIG. 4, a simplified schematic of a wireless control unit 102 for use with the system of FIG. 1 is shown. A microcontroller 402 may be powered by mains power 408 and/or battery 406. The microcontroller 402 may be, or may be based on, a PIC32MM0256GPM064T device. In other embodiments, the microcontroller is any programmable device capable of executing the functions described herein.

The battery 406 may be a single-use or a rechargeable battery. The battery 406 may be used as a backup to the main power 408. The microcontroller 402 monitors data from the pads and can sound alarms (lights or audible alarms) and pass data to another system (such as a computer or nurses' station). For example, an alarm may be generated if a pad 104 becomes unoccupied. An alarm may also be generated if a paired pad 104 does not respond in a predetermined time frame. An alarm may be generated if the pad 104 is not communicating with the microcontroller 402.

The microcontroller 402 may utilize a wireless transceiver unit 406 for wireless communication, particularly the MiWi based or low power communications with the pads 104. The wireless transceiver 406 may be, or may be based on, a Microchip AT86RF212B device. In other embodiments, the wireless transceiver 406 is any device capable of utilizing the wireless communication protocols and functions described herein. In one embodiment, wireless transceiver 406 may be any type of electronic device that communicates wirelessly, e.g., cell phones, iPads, computers, or other electronic device. The transceiver 406, in addition to implementing MiWi communication or other lower power communication with the pads may have WiFi, ethernet, Bluetooth, and other communication hardware and protocols at its disposal for programming, communication, etc. In a further embodiment, functions of the microcontroller 402 and the wireless transceiver 406 may be integrated on the same chip or device.

The wireless control unit 102 may also provide an input/output block 404. This may include buttons, indicator lights, speaker, screens, wireless or wired ports, and other communication mechanisms.

Figure 5:
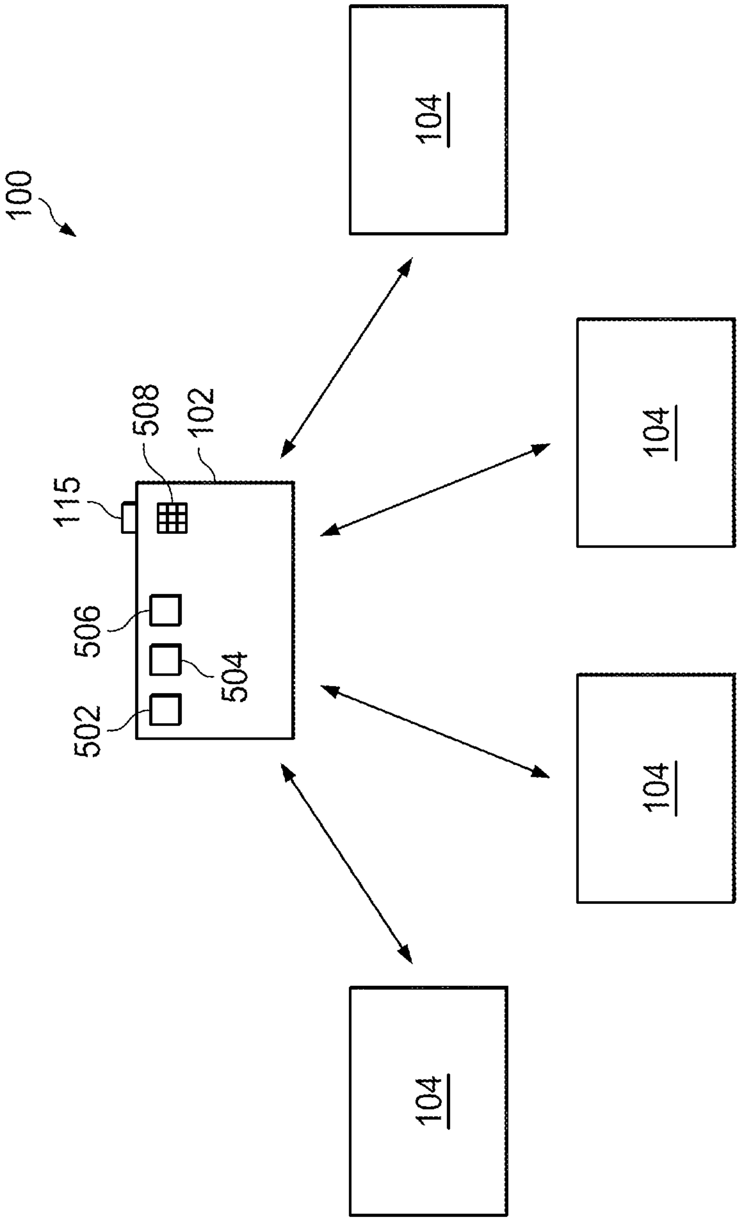
FIG. 5 is a diagram of an exemplary network topology of the system of FIG. 1.

Referring now to FIG. 5, a diagram of an exemplary network topology of the system of FIG. 1 is shown. The wireless control unit 102 may have wireless one-way or two-way communication with multiple pads 104. As part of the IO Block, the wireless control unit 102 may provide a power button 502, a reset or white-listing button 504, a pairing mode button 506, and others. A speaker 508 may be provided for sounding audible alarms.

Although the examples above are given in a scenario where the wireless control unit 102 is in the same room as the pads 104, other embodiments may differ. For example, the wireless control unit 102 may be placed outside the patient room, or placed in a location such that the control unit 102 is not visible to the patient. In such case, in addition to, or instead of lighting the room with light 115 (or another light) when a patient leaves a pad 104, the wireless control unit 102 may provide an alarm light visible outside the room (for example, above a patient room door) or with light 115 now located outside the patient room. In this manner, the wireless control unit 102 can be removed from a patient's proximity for medical reasons, but still usefully monitor the pad(s) 104. The light 115 may also provide different colors, for example white or red. When used as part of an alert, the light 115 can also remain on steadily, or may flash for greater visibility.

A wireless pairing process is provided herein. A new pad 104 (e.g., an unused or unpaired pad), upon being detected within predetermined radius of the wireless control unit 102, may be available for pairing. According to embodiments of the present disclosure, it is not necessary to place an unpaired pad 104 immediately next to the wireless control unit 102. The wireless control unit 102 may detect unpaired pads 104 within its wireless range and offer to a user to pair the same. In various embodiments, the wireless range of the system 100 (e.g., between the pads 104 and control unit 102) is at least the size of a typical hospital room. In various embodiments, the wireless range may be 20 feet, 30 feet, 40 feet, or more. The wireless control unit 102 may be able to discriminate between pads paired to itself, unpaired pads, and pads paired to another device (e.g., a similar unit in an adjacent or nearby room).

In operation, initially, the controller 102 may be in an unconfigured state. It will not have any previously white-listed mats or pads 104 connected to it, and it will not have a wireless control ID or a PAN ID. It will send an "Active Scan" request to identify other networks in the area, and to identify the channel that has the lowest energy or controller 102 will identify what low frequency band should be used to communicate with pads 104 and other wireless products so as to not cause interference with other devices, including other medical communicating devices.

Once it has identified any other wireless controllers in the area with their PAN IDs, this controller 102 may randomly select a PAN ID that does not collide with an existing PAN ID. It will also select the channel that shows the lowest power/noise level. Once the controller 102 has selected a PAN ID and channel, it will maintain this PAN ID and channel until it is reconfigured.

Figure 6:
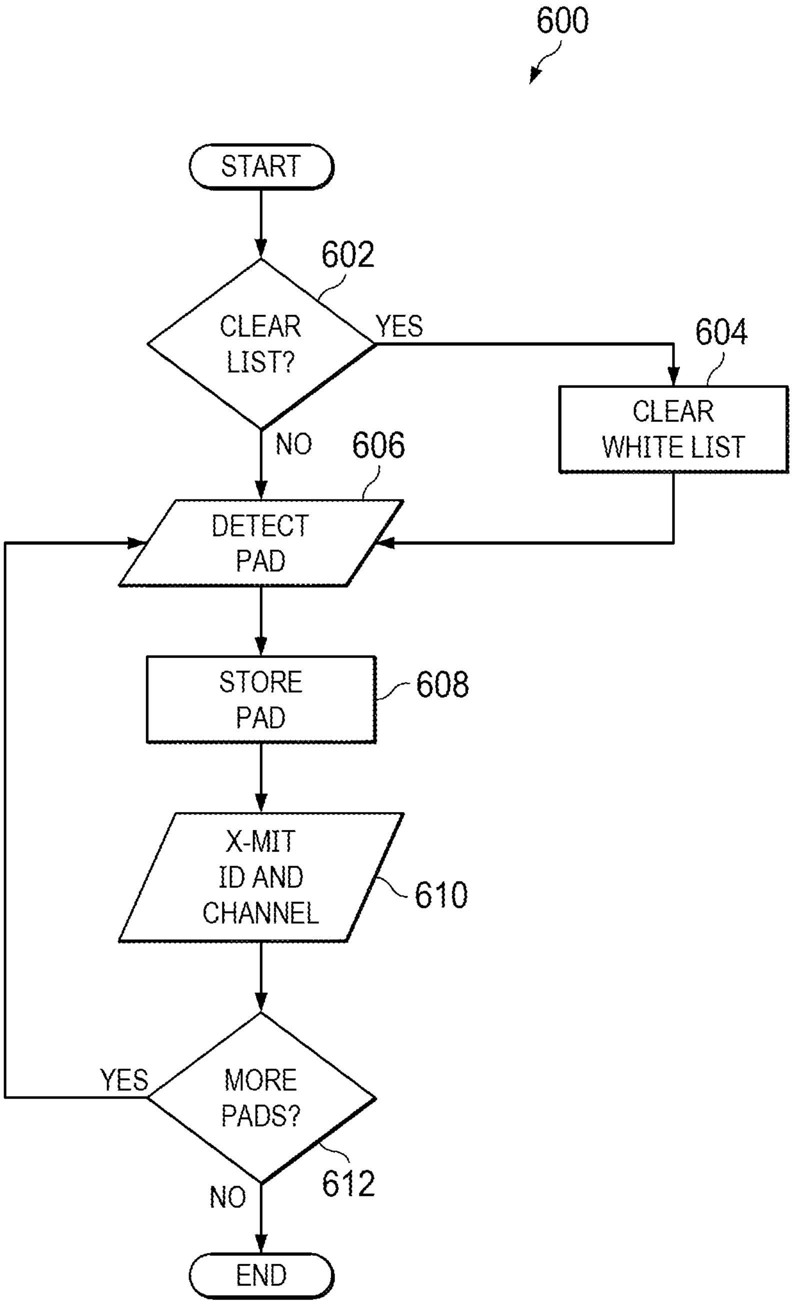
FIG. 6 is a flow chart indicating a pairing process for a wireless control unit according to aspects of the present disclosure.

Referring now to FIG. 6, a flow chart 600 indicating a pairing process for a wireless control unit 102 according to aspects of the present disclosure is shown. The controller 102 may have two pairing modes: a "clear white-list and pair" pairing mode (e.g., state "PAIR.0"), and a "pair additional devices" mode (e.g. state "PAIR.1"). If the clear white-list mode is selected at step 602, the white list of any previously paired pads is erased from the control unit at step 604.

Whether the white list is previously cleared, the following process may be performed to pair a new pad 104 with a controller 102 that has established its PAN ID and operating channel. The controller 102 will be put into a pairing mode, to look for new pads as shown at step 606. The pad 104 itself will be put into a closed state (e.g., switches 208 closed). The pad 104 will then power up and send a connection request signal (e.g., 0x81 "P2P Connection Request" command), with PAN ID destination address (e.g., 0xFFFF broadcast) and device destination address (e.g., 0xFFFF broadcast). The control unit detects this signal at step 606 and stores an identification of the pad 104 in the white list at step 608. The controller 102 may audibly beep when it detects the new pad 104 to indicate that the pad 104 was detected.

At step 610 the controller 102 will send a response message (e.g., 0x91 "P2P Connection Response" command). The P2P Connection Response indicates to the mat what PAN ID and device ID to use for subsequent packet transmission. The pad 104 will send a message to the controller indicating its updated state (same message for whether the mat is open or closed, indicating the new state). If the control unit is still in pairing mode, or is placed back in pairing mode, the process returns to step 606.

Figure 7:
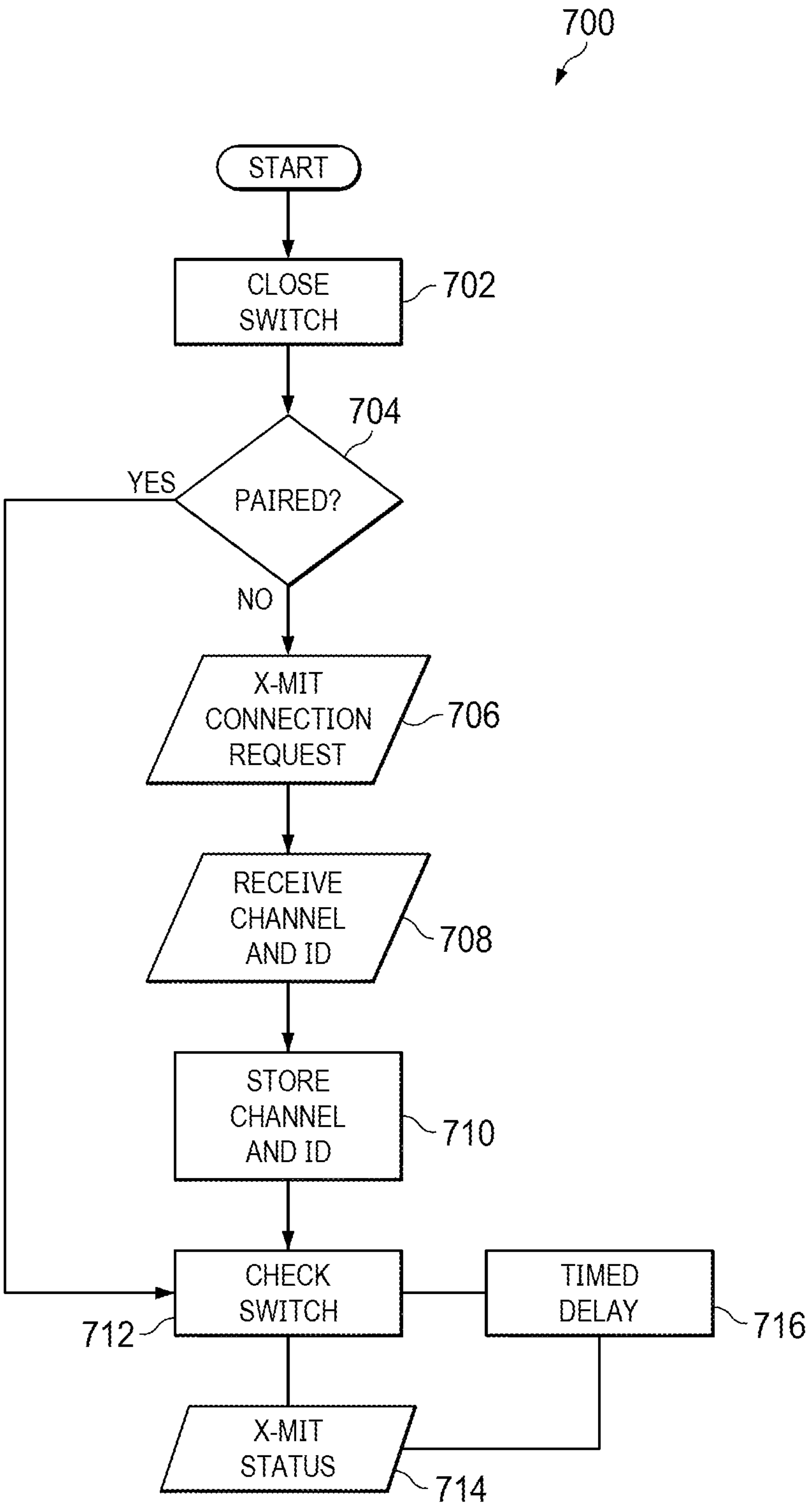
FIG. 7 is a flow chart indicating a pairing operation process of a patient monitoring pad according to aspects of the present disclosure.

Referring now to FIG. 7, a flow chart indicating a pairing operation from the perspective of a pad 104 is shown. At step 702 the switch 210 is closed manually. If the pad 104 is not paired (step 704) the connection request is transmitted at step 706. The channel and ID are received from the control unit 102 at step 708 and stored at step 710. At step 712 the state of the switch 210 (or all switches 210, if applicable) is determined and transmitted at step 712 (using the previously provided ID and channel). A delay may occur at step 716 following which the switch 210 is checked again at step 712.

In effect, once the pad 104 has received both data link layer acknowledgement and application layer acknowledgement, the pad 104 will either turn off, if the new state is now open (e.g., switches 210 open or no patient is present), or go into a low power mode waiting for the switches 210 to open. During normal operation, the pad 104 may undergo the same process even whether the system 100 is in pairing mode or not. In some embodiments, if one or more switch 210 is open, the pad 104 may continuously or repeatedly broadcast the open status. The lower power delay (e.g., timed delay step 716) may only be appropriate where switch 210 or switches 210 if there are multiples switches, are closed (indicating patient presence) and continuous broadcast may be detrimental to battery life.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional elements.

It is to be understood that where the claims or specification refer to "a" or "an" element, such reference is not to be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%.

When, in this document, a range is given as "(a first number) to (a second number)" or "(a first number)-(a second number)", this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range is also intended to include subranges such as 26-100, 27-100, etc., 25-99, 25-98, etc., as well as any other possible combination of lower and upper values within the stated range, e.g., 33-47, 60-97, 41-45, 28-96, etc. Note that integer range values have been used in this paragraph for purposes of illustration only and decimal and fractional values (e.g., 46.7-91.3) should also be understood to be intended as possible subrange endpoints unless specifically excluded.

It should be noted that where reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility).

Further, it should be noted that terms of approximation (e.g., "about", "substantially", "approximately", etc.) are to be interpreted according to their ordinary and customary meanings as used in the associated art unless indicated otherwise herein. Absent a specific definition within this disclosure, and absent ordinary and customary usage in the associated art, such terms should be interpreted to be plus or minus 10% of the base value.

Thus, the present invention is well adapted to carry out the objects and attain the ends and advantages mentioned above as well as those inherent therein. While the inventive device has been described and illustrated herein by reference to certain preferred embodiments in relation to the drawings attached thereto, various changes and further modifications, apart from those shown or suggested herein, may be made therein by those of ordinary skill in the art, without departing from the spirit of the inventive concept the scope of which is to be determined by the following claims.

What is claimed is:

1. A system for monitoring the presence of a patient at a location comprising:

at least one pressure sensitive pad comprising:

at least one internal electrical contact indicating presence of a patient on the pad when the electrical contact is closed;

an internal control circuit electrically connected to at least one contact to detect closure of the contact;

an internal wireless transceiver used by the control circuit to broadcast a signal indicating presence and absence of the patient based on the closure of the at least one contact; and an external cover sealing the at least one internal electrical contact, the internal control circuit, and the internal wireless transceiver together inside the cover; and a wireless control unit receiving the signal broadcast from the at least one pressure sensitive pad and indicating an alarm when the pressure sensitive pad indicates the absence of the patient;

wherein:

the wireless control unit further comprises a microcontroller and a wireless transceiver, the microcontroller receiving the signal broadcast from the at least one pressure sensitive pad via the wireless transceiver and indicating the alarm;

the at least one pressure sensitive pad has a paired state and an unpaired state respecting the wireless control unit; and the at least one pressure sensitive pad, when in the unpaired state, broadcasts a connection request signal when the at least one internal electrical contact is closed.

2. The system of claim 1, wherein the at least one internal electrical contact comprises a plurality of internal electrical contacts.

3. The system of claim 1, further comprising an internal foam layer defining an opening containing the at least one internal electrical contact.

4. The system of claim 1, further comprising an internal battery inside the external cover.

5. The system of claim 1, wherein the external cover does not pass any wires therethrough.

6. The system of claim 1, wherein the wireless control unit has a first pairing mode wherein it receives the connection request signal from the at least one pressure sensitive pad and broadcasts a connection response signal back to the at least one pressure sensitive pad indicating an identification of the wireless control unit and an operating channel.

7. The system of claim 6, wherein the at least one pressure sensitive pad stores the identification of the wireless control unit and the operating channel and enters a sleep mode for a predetermined period of time.

8. The system of claim 7 wherein, after the predetermined period of time, the at least one pressure sensitive pad broadcasts to the wireless control unit the signal indicating presence and absence of the patient based on the closure of the at least one contact using the identification of the wireless control unit and the operating channel.

9. The system of claim 1, wherein the wireless control unit receives signals from multiple pressure sensitive pads, each pressure sensitive pad broadcasting a separate respective signal indicating presence and absence of the patient based on the closure of the at least one internal electrical contact.

10. The system of claim 9, wherein the wireless control unit can be reset to determine an identification of the wireless control unit by selecting a random identification that does not correspond to any identifications received wirelessly from any other wireless controllers.

11. The system of claim 10, wherein the wireless control unit selects a wireless channel for communication with the at least one pressure sensitive pad by scanning available channels and selecting among the available channels with a lowest broadcast energy.

12. The system of claim 1, wherein the alarm comprises an audible alarm.

13. The system of claim 1, wherein the alarm comprises an alert signal sent electronically from the wireless control unit.

14. The system of claim 1, wherein the alarm comprises a visible light.

15. The system of claim 1, wherein the alarm comprises a light visible to the patient.

16. The system of claim 1, further comprising a wireless control unit receiving the signal broadcast from the at least one pressure sensitive pad and illuminating a light in proximity to the patient in response thereto.

17. The system of claim 1 further comprising:

a capacitor in communication with said internal wireless transceiver, said capacitor for storing sufficient energy to permit said internal wireless transceiver to activate an alarm signal.

18. A system for monitoring presence of a patient at a location comprising:

a sealed pressure sensitive pad containing an internal power supply, an internal controller, and an internal contact switch contained in an opening in an internal foam layer such that weight of a patient on the pressure sensitive pad signals presence of the patient to the controller, the controller intermittently broadcasting a signal indicating presence or absence of the patient; and a wireless control unit receiving the signal indicating presence of or absence of the patient and producing an alarm when the signal indicates absence of the patient;

wherein the sealed pressure sensitive pad is impervious to bodily fluids and does not have any external openings for wiring;

wherein the signal indicating absence or presence of a patient is broadcast on a channel and with an identification provided by the wireless control unit;

wherein the sealed pressure sensitive pad has a paired state and an unpaired state respecting the wireless control unit; and wherein the at least one pressure sensitive pad, when in the unpaired state, broadcasts a connection request signal to receive the channel and with an identification when the at least one internal electrical contact is closed.

* * * * *